(12) United States Patent
Kohm et al.

(10) Patent No.: US 8,348,976 B2
(45) Date of Patent: Jan. 8, 2013

(54) SPINOUS-PROCESS IMPLANTS AND METHODS OF USING THE SAME

(75) Inventors: Andrew Kohm, Burlingame, CA (US); Hugues F. Malandain, Mountain View, CA (US); Thomas A. Slater, Mountain View, CA (US)

(73) Assignee: Kyphon SARL, Neuchatel (CH)

( * ) Notice: Subject to any disclaimer, the term of this patent is extended or adjusted under 35 U.S.C. 154(b) by 760 days.

(21) Appl. No.: 11/845,272

(22) Filed: Aug. 27, 2007

(65) Prior Publication Data

US 2009/0062915 A1    Mar. 5, 2009

(51) Int. Cl.
*A61B 17/70* (2006.01)

(52) U.S. Cl. ............................................ 606/248

(58) Field of Classification Search .......... 606/246–249; 623/17.11–17.16
See application file for complete search history.

(56) References Cited

U.S. PATENT DOCUMENTS

| | | | |
|---|---|---|---|
| 2,677,369 A | 5/1954 | Knowles | |
| 3,648,691 A | 3/1972 | Lumb et al. | |
| 4,011,602 A | 3/1977 | Rybicki et al. | |
| 4,257,409 A | 3/1981 | Bacal et al. | |
| 4,554,914 A | 11/1985 | Kapp et al. | |
| 4,573,454 A | 3/1986 | Hoffman | |
| 4,604,995 A | 8/1986 | Stephens et al. | |
| 4,686,970 A | 8/1987 | Dove et al. | |
| 4,827,918 A | 5/1989 | Olerud | |
| 5,011,484 A | 4/1991 | Breard | |
| 5,047,055 A | 9/1991 | Bao et al. | |
| 5,092,866 A | 3/1992 | Breard et al. | |
| 5,201,734 A | 4/1993 | Cozad et al. | |
| 5,306,275 A | 4/1994 | Bryan | |
| 5,360,430 A | 11/1994 | Lin | |
| 5,366,455 A | 11/1994 | Dove | |
| 5,415,661 A | 5/1995 | Holmes | |
| 5,437,672 A | 8/1995 | Alleyne | |
| 5,454,812 A | 10/1995 | Lin | |

(Continued)

FOREIGN PATENT DOCUMENTS

DE    2821678 A1    11/1979

(Continued)

OTHER PUBLICATIONS

"Dispositivo Intervertebrale Ammortizzante DIAM," date unknown, p. 1.

(Continued)

*Primary Examiner* — Alvin Stewart
*Assistant Examiner* — Steven Cotroneo
(74) *Attorney, Agent, or Firm* — Dilworth & Barrese, LLP

(57) ABSTRACT

Devices and methods for performing a procedure within a spine are disclosed herein. In one embodiment, a method includes coupling a first implant to a pedicle of a first vertebra of a spinal column such that at least a portion of the first implant is disposed between a first spinous process and a second spinous process of the spinal column. A second implant is coupled to a pedicle of a second vertebra of the spinal column. At least a portion of an outer surface of the first implant is configured to contact at least a portion of an outer surface of the second implant when the spinal column is in extension. The outer surface of the first implant and the outer surface of the second implant being at a spaced distance from each other when the spinal column is in flexion.

12 Claims, 10 Drawing Sheets

U.S. PATENT DOCUMENTS

| | | | |
|---|---|---|---|
| 5,496,318 A | 3/1996 | Howland et al. | |
| 5,609,634 A | 3/1997 | Voydeville | |
| 5,628,756 A | 5/1997 | Barker, Jr. et al. | |
| 5,645,599 A | 7/1997 | Samani | |
| 5,674,295 A | 10/1997 | Ray et al. | |
| 5,676,702 A | 10/1997 | Ratron | |
| 5,690,649 A | 11/1997 | Li | |
| 5,702,452 A | 12/1997 | Argenson et al. | |
| 5,810,815 A | 9/1998 | Morales | |
| 5,836,948 A | 11/1998 | Zucherman et al. | |
| 5,860,977 A | 1/1999 | Zucherman et al. | |
| 5,976,186 A | 11/1999 | Bao et al. | |
| 6,022,376 A | 2/2000 | Assell et al. | |
| 6,048,342 A | 4/2000 | Zucherman et al. | |
| 6,068,630 A | 5/2000 | Zucherman et al. | |
| 6,132,464 A * | 10/2000 | Martin | 623/17.15 |
| 6,293,949 B1 | 9/2001 | Justis et al. | |
| 6,352,537 B1 | 3/2002 | Strnad | |
| 6,364,883 B1 | 4/2002 | Santilli | |
| 6,402,750 B1 | 6/2002 | Atkinson et al. | |
| 6,440,169 B1 | 8/2002 | Elberg et al. | |
| 6,451,019 B1 | 9/2002 | Zucherman et al. | |
| 6,582,433 B2 | 6/2003 | Yun | |
| 6,610,091 B1 * | 8/2003 | Reiley | 623/17.11 |
| 6,626,944 B1 | 9/2003 | Taylor | |
| 6,645,207 B2 | 11/2003 | Dixon et al. | |
| 6,695,842 B2 | 2/2004 | Zucherman et al. | |
| 6,709,435 B2 | 3/2004 | Lin | |
| 6,723,126 B1 | 4/2004 | Berry | |
| 6,733,534 B2 | 5/2004 | Sherman | |
| 6,761,720 B1 | 7/2004 | Senegas | |
| 6,835,205 B2 | 12/2004 | Atkinson et al. | |
| 6,946,000 B2 | 9/2005 | Senegas et al. | |
| 7,011,685 B2 | 3/2006 | Arnin et al. | |
| 7,041,136 B2 | 5/2006 | Goble et al. | |
| 7,048,736 B2 | 5/2006 | Robinson et al. | |
| 7,087,083 B2 | 8/2006 | Pasquet et al. | |
| 7,101,375 B2 | 9/2006 | Zucherman et al. | |
| 7,163,558 B2 | 1/2007 | Senegas et al. | |
| 7,201,751 B2 * | 4/2007 | Zucherman et al. | 606/249 |
| 7,238,204 B2 | 7/2007 | Le Couedic et al. | |
| 7,303,562 B2 | 12/2007 | Cavagna et al. | |
| 7,306,628 B2 | 12/2007 | Zucherman et al. | |
| 7,377,942 B2 | 5/2008 | Berry | |
| 7,442,208 B2 | 10/2008 | Mathieu et al. | |
| 7,445,637 B2 | 11/2008 | Taylor | |
| 2002/0143331 A1 | 10/2002 | Zucherman et al. | |
| 2003/0153915 A1 | 8/2003 | Nekozuka et al. | |
| 2004/0097931 A1 | 5/2004 | Mitchell | |
| 2005/0010293 A1 | 1/2005 | Zucherman et al. | |
| 2005/0049708 A1 | 3/2005 | Atkinson et al. | |
| 2005/0165398 A1 | 7/2005 | Reiley | |
| 2005/0203512 A1 | 9/2005 | Hawkins et al. | |
| 2005/0203624 A1 | 9/2005 | Serhan et al. | |
| 2005/0228391 A1 | 10/2005 | Levy et al. | |
| 2005/0261768 A1 | 11/2005 | Trieu | |
| 2005/0277931 A1 | 12/2005 | Sweeney et al. | |
| 2005/0288672 A1 * | 12/2005 | Ferree | 606/61 |
| 2006/0004358 A1 | 1/2006 | Serhan et al. | |
| 2006/0004447 A1 | 1/2006 | Mastrorio et al. | |
| 2006/0015181 A1 | 1/2006 | Elberg | |
| 2006/0036240 A1 | 2/2006 | Colleran et al. | |
| 2006/0036244 A1 | 2/2006 | Spitler et al. | |
| 2006/0036246 A1 | 2/2006 | Carl et al. | |
| 2006/0052784 A1 | 3/2006 | Dant et al. | |
| 2006/0052786 A1 | 3/2006 | Dant et al. | |
| 2006/0058787 A1 | 3/2006 | David | |
| 2006/0058789 A1 | 3/2006 | Kim et al. | |
| 2006/0058790 A1 | 3/2006 | Carl et al. | |
| 2006/0064165 A1 * | 3/2006 | Zucherman et al. | 623/17.11 |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0085070 A1 | 4/2006 | Kim | |
| 2006/0085074 A1 | 4/2006 | Raiszadeh | |
| 2006/0089654 A1 | 4/2006 | Lins et al. | |
| 2006/0089719 A1 | 4/2006 | Trieu | |
| 2006/0106381 A1 * | 5/2006 | Ferree et al. | 606/61 |
| 2006/0106397 A1 | 5/2006 | Lins | |
| 2006/0111728 A1 | 5/2006 | Abdou | |
| 2006/0122620 A1 | 6/2006 | Kim | |
| 2006/0136060 A1 | 6/2006 | Taylor | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0235387 A1 | 10/2006 | Peterman | |
| 2006/0235532 A1 | 10/2006 | Meunier et al. | |
| 2006/0241613 A1 | 10/2006 | Brueneau et al. | |
| 2006/0247623 A1 | 11/2006 | Anderson et al. | |
| 2006/0247640 A1 | 11/2006 | Blackwell et al. | |
| 2006/0264938 A1 | 11/2006 | Zucherman et al. | |
| 2006/0271044 A1 | 11/2006 | Petrini et al. | |
| 2006/0271049 A1 | 11/2006 | Zucherman et al. | |
| 2006/0293662 A1 * | 12/2006 | Boyer et al. | 606/61 |
| 2006/0293663 A1 | 12/2006 | Walkenhorst et al. | |
| 2007/0043362 A1 | 2/2007 | Malandain et al. | |
| 2007/0162000 A1 | 7/2007 | Perkins | |
| 2007/0198091 A1 | 8/2007 | Boyer et al. | |
| 2007/0233068 A1 | 10/2007 | Bruneau et al. | |
| 2007/0233081 A1 | 10/2007 | Pasquet et al. | |
| 2007/0233089 A1 * | 10/2007 | DiPoto et al. | 606/61 |
| 2007/0270834 A1 | 11/2007 | Bruneau et al. | |
| 2008/0161818 A1 | 7/2008 | Kloss et al. | |

FOREIGN PATENT DOCUMENTS

| | | |
|---|---|---|
| EP | 0322334 B1 | 2/1992 |
| EP | 2799948 A1 | 4/2001 |
| EP | 1138268 A1 | 10/2001 |
| EP | 1330987 A1 | 7/2003 |
| FR | 2623085 A1 | 5/1989 |
| FR | 1484348 A1 | 6/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2816197 A1 | 5/2002 |
| JP | 02-224660 | 9/1990 |
| JP | 09-075381 | 3/1997 |
| SU | 988281 | 1/1983 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | WO 2005/009300 A1 | 2/2005 |
| WO | WO 2005/044118 A1 | 5/2005 |
| WO | WO 2005/110258 A1 | 11/2005 |
| WO | WO 2006/064356 A1 | 6/2006 |
| WO | WO 2007/034516 A1 | 3/2007 |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," Spine, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumata, Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," Spine, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," Spine, 1991, pp. S298-S301, vol. 16, No. 6, Supplement.

* cited by examiner

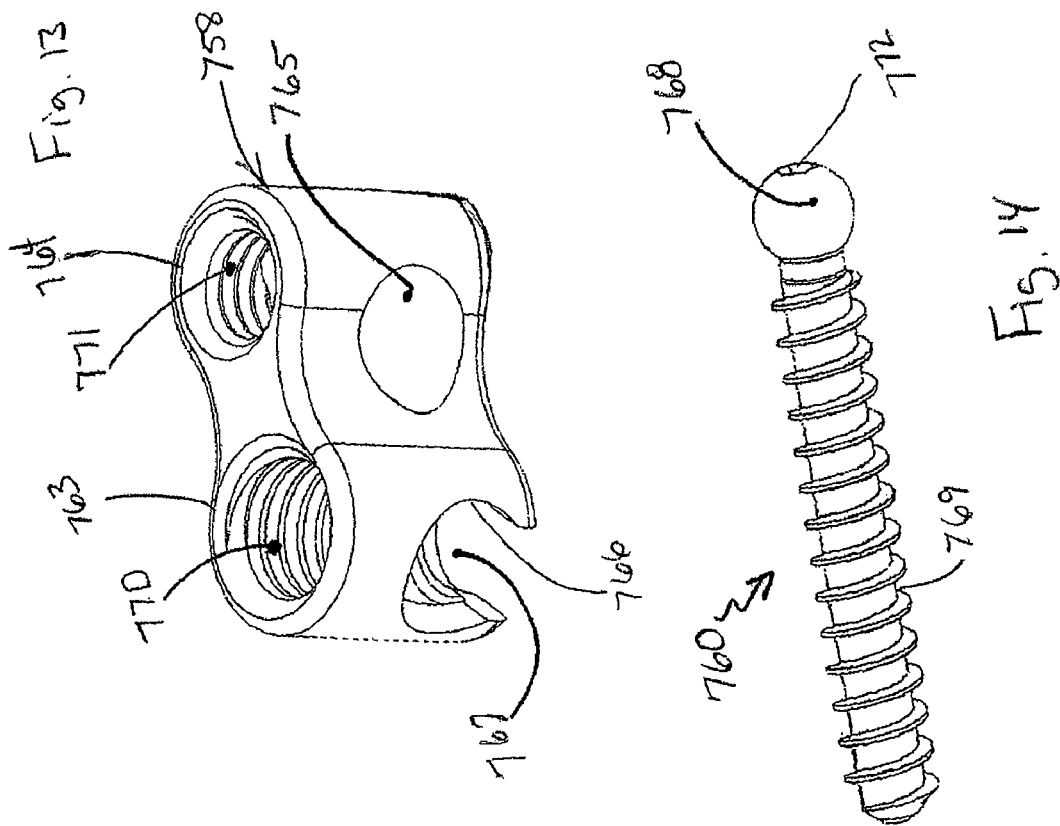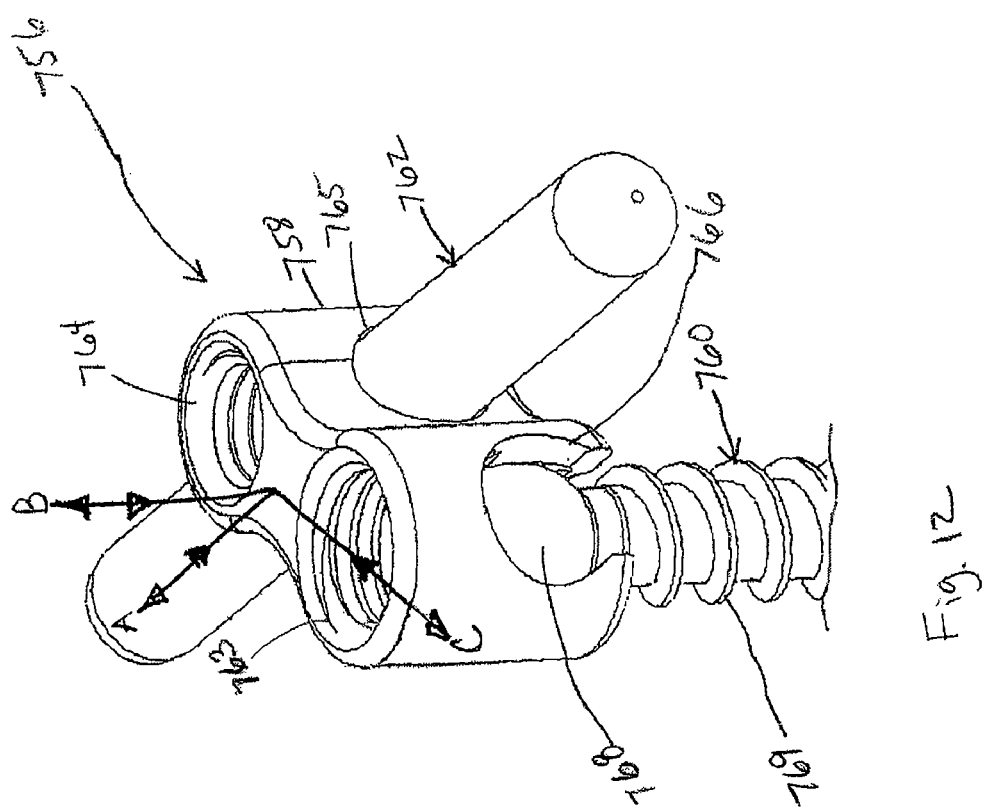

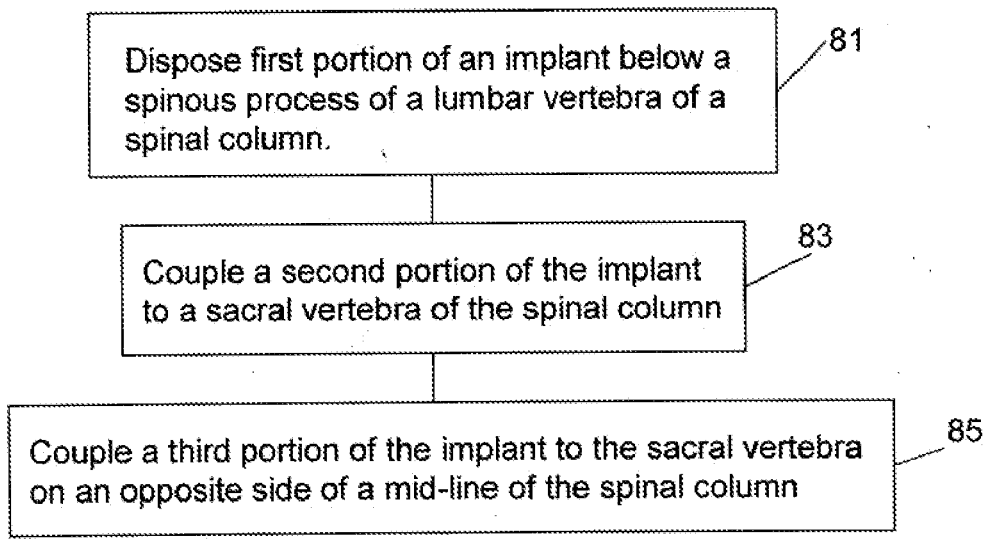

SPINOUS-PROCESS IMPLANTS AND METHODS OF USING THE SAME

BACKGROUND

The invention relates generally to medical devices and procedures, including, for example, medical devices and methods to treat spinal conditions using spinal implants that can be implanted between adjacent spinous processes.

A back condition that impacts many individuals is spinal stenosis. Spinal stenosis is a progressive narrowing of the spinal canal that causes compression of the spinal cord. Each vertebra in the spinal column has an opening that extends through and is aligned vertically with other vertebra openings to form the spinal canal. The spinal cord runs through the spinal canal. As the spinal canal narrows, the spinal cord and nerve roots extending from the spinal cord and between adjacent vertebrae are compressed and may become inflamed. Spinal stenosis can cause pain, weakness, numbness, burning sensations, tingling, and in particularly severe cases, may cause loss of bladder or bowel function, or paralysis. The legs, calves and buttocks are most commonly affected by spinal stenosis, however, the shoulders and arms may also be affected.

Mild cases of spinal stenosis may be treated with rest or restricted activity, non-steroidal anti-inflammatory drugs (e.g., aspirin), corticosteroid injections (epidural steroids), and/or physical therapy. Some patients find that bending forward, sitting or lying down may help relieve the pain. This may be due to the fact that bending forward creates more vertebral space, which may temporarily relieve nerve compression. Because spinal stenosis is a progressive disease, the source of pressure may have to be surgically corrected (e.g., decompressive laminectomy) as the patient has increasing pain. The surgical procedure can remove bone and other tissues that have impinged upon the spinal canal or put pressure on the spinal cord. Two adjacent vertebrae may also be fused during the surgical procedure to correct an area of instability, improper alignment or slippage, such as that caused by spondylolisthesis. Surgical decompression can relieve pressure on the spinal cord or spinal nerve by widening the spinal canal to create more space. This procedure requires that the patient be given a general anesthesia and an incision is made in the patient to access the spine to remove the areas that are contributing to the pressure. This procedure, however, may result in blood loss and an increased chance of significant complications, and usually results in an extended hospital stay.

Some known procedures involve the implantation of a device (e.g., an interspinous process implant) between the adjacent spinous processes to limit the extension. Some devices are coupled directly to a spinous process, while others are placed between adjacent spinous processes and are configured to maintain their position therebetween.

SUMMARY OF THE INVENTION

Devices and methods for performing a procedure within a spine are disclosed herein. In one embodiment, a method includes coupling a first implant to a pedicle of a first vertebra of a spinal column such that at least a portion of the first implant is disposed between a first spinous process associated with the first vertebra and a second spinous process associated with a second vertebra of the spinal column. A second implant is coupled to a pedicle of the second vertebra of the spinal column. At least a portion of an outer surface of the first implant is configured to contact at least a portion of an outer surface of the second implant when the spinal column is in extension. The outer surface of the first implant and the outer surface of the second implant being at a spaced distance from each other when the spinal column is in flexion. In another embodiment, a method includes disposing a first portion of an implant below a spinous process of a lumbar vertebra of a spinal column. A second portion of the implant is coupled to a sacral vertebra of the spinal column and the implant is configured to limit extension of the spinal column.

BRIEF DESCRIPTION OF THE DRAWINGS

FIG. 12 is a side perspective view of a portion of a fusion device according to an embodiment of the invention.

FIG. 13 is a side perspective view of a coupler according to an embodiment of the invention.

FIG. 14 is a side view of a coupling member according to an embodiment of the invention.

FIGS. 16-18 are each flowcharts illustrating a method according to different embodiments of the invention.

DETAILED DESCRIPTION

Figure 1:
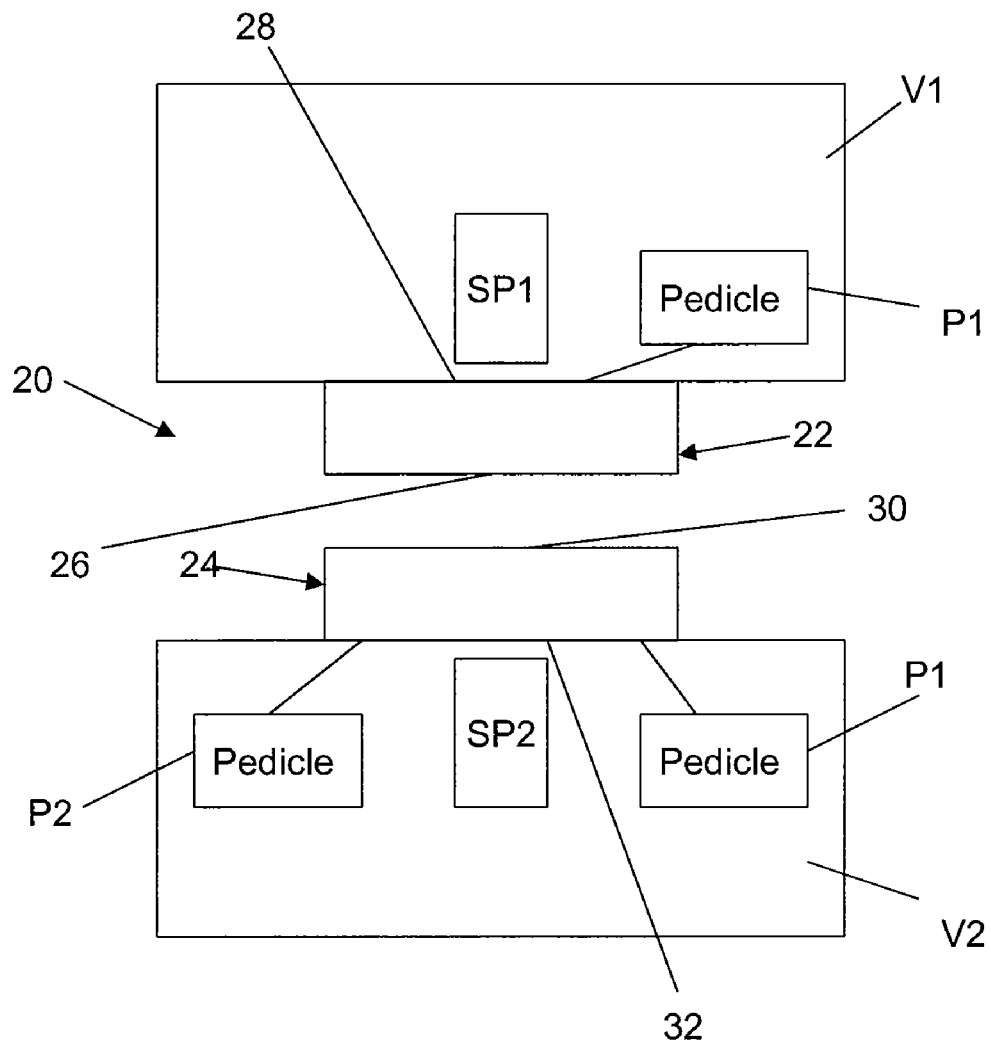
FIG. 1 is a schematic illustration of a medical device according to an embodiment of the invention shown coupled to a schematic representation of a portion of a spine.

Devices and methods for performing medical procedures within a spine are disclosed herein. In one embodiment, an apparatus includes an interspinous-process implant (also referred to herein as "implant") that can be placed between adjacent spinous processes and coupled to a pedicle. In another embodiment, two implants are inserted between adjacent spinous processes, with each being coupled to a pedicle of a vertebra. Such implants can be coupled to a single pedicle of the vertebra, or to a first pedicle of the vertebra on one side of a spinous process and to a second pedicle of the vertebra on an opposite side of the spinous process. In some embodiments, the implant is coupled to a sacral vertebra and can include a surface configured to contact a spinous process of a} lumbar vertebra. For example, an implant can be positioned at least partially beneath a spinous process of the L5 lumbar vertebra and be coupled to the S1 sacral vertebra.

The implants described herein can include one or more surfaces that can contact a surface of a spinous process during movement of the spinal column. For example, in some embodiments, an implant can be disposed between adjacent spinous processes and include a surface configured to contact one of the adjacent spinous processes. In another embodiment, an implant can be disposed between adjacent spinous processes and include a first surface configured to contact a first spinous process and a second surface configured to contact a second adjacent spinous process. In some embodiments, a first implant has a surface that can contact a surface of a second implant when both of the implants are disposed between adjacent spinous processes and coupled to one or more pedicles of a vertebra.

One or more implants disposed between adjacent spinous processes can function as an extension-limiting device when the spinal column is in extension to limit the extension of the spinal column. For example, in some embodiments, first and second implants can contact each other when the spinal column is in extension to limit the amount of extension, and be at a spaced distance from each other during flexion of the spinal column. Thus, when the implants are coupled between adjacent spinous processes, flexion of the spinal column can still occur because the implants do not fixedly couple the adjacent vertebrae to each other.

The implants described herein can also be used to off-load forces exerted from one level to a lower level of the spinal column. For example, the implants can be fixedly coupled to a pedicle of a vertebra such that a force exerted on the implant can be transferred to the pedicle rather than to the lower-level spinous process. The implants can alternatively be pivotally coupled to a pedicle of a vertebra such that the implant can move or pivot relative to the vertebra and move when contacted by a different-level spinous process during movement of the spinal column. In some embodiments, the implant is formed with a material that allows the implant to move or flex when contacted by a spinous process.

The implants described herein can also be used in conjunction with a fusion device to provide a more gradual variation of the stiffness of the spine, and can also be used to limit the extension of the spine at a particular level. A level, as referred to herein, means a region of the spinal column encompassing a pair of adjacent vertebra or a pair of spinous processes. For example, a first level can include a spinous process of a first vertebra and a spinous process of a second vertebra inferior to the first vertebra. A second level can be the second vertebra and a third vertebra inferior to the second vertebra.

In one embodiment, a method includes coupling a first implant to a pedicle of a first vertebra of a spinal column such that at least a portion of the first implant is disposed between a first spinous process and a second spinous process of the spinal column. A second implant is coupled to a pedicle of a second vertebra of the spinal column. At least a portion of an outer surface of the first implant is configured to contact at least a portion of an outer surface of the second implant when the spinal column is in extension. The outer surface of the first implant and the outer surface of the second implant being at a spaced distance from each other when the spinal column is in flexion.

In another embodiment, a method includes disposing a first portion of an implant below a spinous process of a lumbar vertebra of a spinal column. A second portion of the implant is coupled to a sacral vertebra of the spinal column. The implant is configured to limit extension of the spinal column when the second portion of the implant is coupled to the sacral vertebra and the first portion of the implant is disposed beneath the spinous process.

In one embodiment, an apparatus includes an implant configured to be coupled only to a single pedicle of a first vertebra of a spinal column such that at least a portion of the implant is disposed between a first spinous process of the first vertebra and a second spinous process of an adjacent second vertebra of the spinal column.

In another embodiment, an apparatus includes a first implant configured to be coupled to a pedicle of a first vertebra of a spinal column. The first implant has an outer surface configured to be disposed between a first spinous process of the first vertebra and a second spinous process of an adjacent second vertebra of the spinal column. A second implant is configured to be coupled to a pedicle of the second vertebra of the spinal column. At least a portion of the second implant being configured to be disposed between the first spinous process and the second spinous process. At least a portion of the outer surface of the first implant is configured to contact least a portion of an outer surface of the second implant when the spinal column is in extension.

In another embodiment, a method includes disposing a first portion of an implant beneath a spinous process of a first vertebra of a spinal column. A second portion of the implant is coupled to a second vertebra of the spinal column adjacent the first vertebra. A first portion of a fusion device is coupled to the second portion of the implant, and a second portion of the fusion device is coupled to a third vertebra of the spinal column adjacent the second vertebra.

It is noted that, as used in this written description and the appended claims, the singular forms "a," "an" and "the" include plural referents unless the context clearly dictates otherwise. Thus, for example, the term "a lumen" is intended to mean a single lumen or a combination of lumens. Furthermore, the words "proximal" and "distal" refer to direction closer to and away from, respectively, an operator (e.g., surgeon, physician, nurse, technician, etc.) who would insert the medical device into the patient, with the tip end (i.e., distal end) of the device inserted inside a patient's body. Thus, for example, the catheter end inserted inside a patient's body would be the distal end of the catheter, while the catheter end outside a patient's body would be the proximal end of the catheter.

As used herein the term "sacral vertebra" refers to a vertebra associated with a sacrum of a spinal column. For example, the sacrum includes five vertebra fused together, referred to as the S1, S2, S3, S4, and S5 sacral vertebrae. The S1 sacral vertebra is superior to the S2 sacral vertebra, the S2 sacral vertebra is superior to the S3 sacral vertebra and so on. As used herein the term "lumbar vertebra" refers to the L1-L5 vertebrae of the spinal column, with the L5 lumbar vertebra being superior to the S1 sacral vertebra, the L4 lumbar vertebra being superior to the L5 vertebra, the L3 vertebra being superior to the L4 vertebra and so on. As used herein, the terms "vertebra" and "vertebrae" used without a modifier can refer to any type of vertebra or vertebrae (e.g., sacral, lumbar, thoracic, cervical).

FIG. 1 is a schematic illustration of an example of a medical device that can be used to perform the methods described herein. A medical device 20 can be used, for example, to perform minimally-invasive surgical procedures such as a percutaneous medical procedure within, for example, a spinal column. The medical device 20 can include a first implant 22 that can be disposed at least partially beneath a spinous process SP1 of a spinal column, and second implant 24 that can be disposed at least partially above an adjacent spinous process SP2 of the spinal column.

The first implant 22 and the second implant 24 can each be coupled to one or more pedicles of a vertebra. In some embodiments, the first implant 22 is coupled to a single pedicle P1 of a vertebra V1, and the second implant 24 is coupled to a pedicel P1 and a pedicle P2 of a vertebra V2. FIG. 1 is merely an example of one combination of implants and coupling locations. For example, in other embodiments, the first implant 22 can be coupled to a pedicle of the vertebra V2 and/or the second implant 24 can be coupled to the vertebra V1. In some embodiments, the first implant 22 is also coupled to a second pedicle (not shown) on the vertebra V1. The vertebra V1 and the vertebra V2 can be any adjacent vertebrae within a spinal column. For example, the vertebra V1 can be a lumbar vertebra and the vertebra V2 can be a sacral vertebra. In some embodiments, an implant can be disposed between a spinous process of the L4 lumbar vertebra and a spinous process of the L5 lumbar vertebra, and coupled to the L5 lumbar vertebra and/or the S1 sacral vertebra.

The first implant 22 includes an outer surface 26 and an outer surface 28. The second implant 24 includes an outer surface 30 and a second outer surface 32. In the embodiment shown in FIG. 1, at least a portion of the outer surface 26 of the first implant 22 and at least a portion of the outer surface 30 of the second implant 24 can be configured such that during movement of the spinal column, the outer surface 26 and the outer surface 30 can move into and out of contact with each other. In such an embodiment, during movement of the spine, the outer surface 26 and the outer surface 30 can sometimes be in contact with each other, and at other times be at a spaced distance from each other. For example, during extension of the spinal column, the outer surface 26 and the outer surface 30 can contact each other and limit further extension of the spinous processes SP1 and SP2 (e.g. movement toward each other). During flexion of the spinal column, the outer surface 26 and the outer surface 30 can be at a spaced distance from each other. Thus, the first implant 22 and the second impact member 24 can limit the extension of the spinous processes SP1 and SP2, but not limit the flexion, lateral bending, or axial rotation of the spinous processes SP1 and SP2 relative to each other or with respect to the spinal column during movement of the spinal column.

The outer surface 28 of the first implant 22 and the outer surface 32 of the second implant 24 can each be configured to move into and out of contact with the spinous process SP1 and the spinous process SP2, respectively, during movement of the spinal column. In such an embodiment, during movement of the spine, the outer surface 28 and the outer surface 32 can sometimes be in contact with their respective spinous process SP1 and SP2, and at other times be at a spaced distance from their respective spinous process SP1 and SP2. For example, during extension of the spinal column, the outer surface 28 and the outer surface 32 can each contact their respective spinous process SP1 and SP2 and during flexion of the spinal column, the outer surface 28 and the outer surface 32 can each be at a spaced distance from their respective spinous process SP1 and SP2.

The implants 22 and 24 can each be coupled to a pedicle of a vertebra using a variety of different coupling methods. In addition, each of the first implant 22 and the second implant 24 can include the same coupling configurations or have different coupling configurations. In some embodiments, the first implant 22 and/or the second implant 24 can define one or more openings through which a screw, nail, pin, or other fastening device can be inserted, and coupled to a pedicle. In other embodiments, the first implant 22 and/or the second implant 24 can include a protrusion or spike that can be driven into the pedicle.

As described below with reference to specific example embodiments, the medical device 20 can include a single implant (e.g. 22 or 24). In such an embodiment, the implant can include an outer surface configured to contact a spinous process during movement of the spinal column. In some embodiments, the implant can include a first surface configured to contact a first spinous process and a second surface configured to contact an adjacent second spinous process. A single implant can be coupled to one or more pedicles of a vertebra. For example, the implant can be coupled to a single pedicle P1 of a vertebra V1 as shown for implant 22 in FIG. 1. In some embodiments, a single implant can be coupled to two pedicles of a vertebra. For example, the implant can be coupled to a first pedicle P1 and a second pedicle P2 of a vertebra V2 as shown for implant 24 in FIG. 1. In some embodiments, an implant can be disposed such that a surface of the implant can contact a spinous process of a first vertebra and be coupled to a pedicle of an adjacent second vertebra.

The implants described herein can also be a variety of different shapes and sizes. For example, an implant can have a height that corresponds to the amount of extension limiting desired for a particular patient. If the implant is formed with a flexible material, the height may not need to be as large as when the implant is formed with a rigid material. A thickness (posterior-to-anterior depth) of an implant can be sufficient to maintain the integrity at the coupling to a pedicle, for example, using a pedicle screw. A length of an implant (lateral extent of implant from midline of spinal column) can be sufficient to maintain the position of at least a portion of the implant between adjacent spinous processes.

In some cases, more than two implants may be desired. For example, a procedure can include the insertion of one or more implants between a first spinous process and a second spinous process, one or more implants disposed between the second spinous process and a third spinous process, and one or more implants disposed between the third spinous process and a fourth spinous process. In such a case, various combinations and configurations of the implants can be used. Other quantities of implants can alternatively be used, depending on the particular medical condition and the type of treatment desired.

Having described above various general examples, several examples of specific embodiments are now described. These embodiments are only examples, and many other configurations of a medical device 20 are contemplated.

Figure 2:
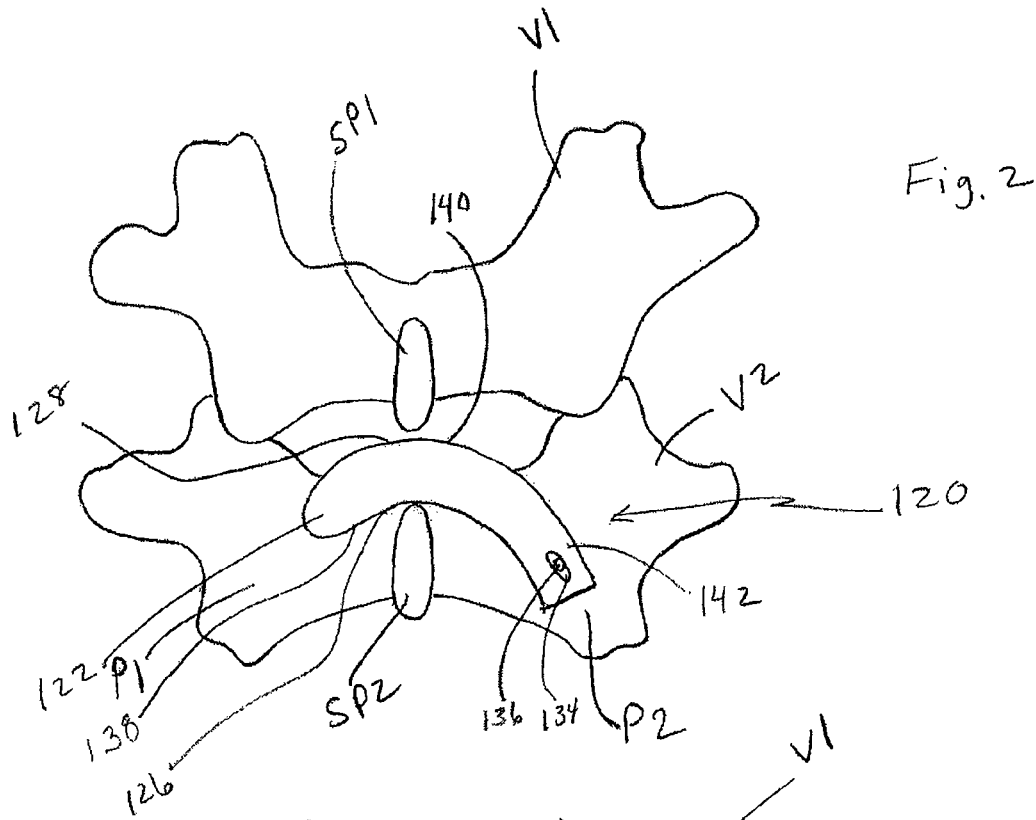
FIG. 2 is a posterior view of a portion of a spinal column and an implant according to an embodiment of the invention.
Figure 3:
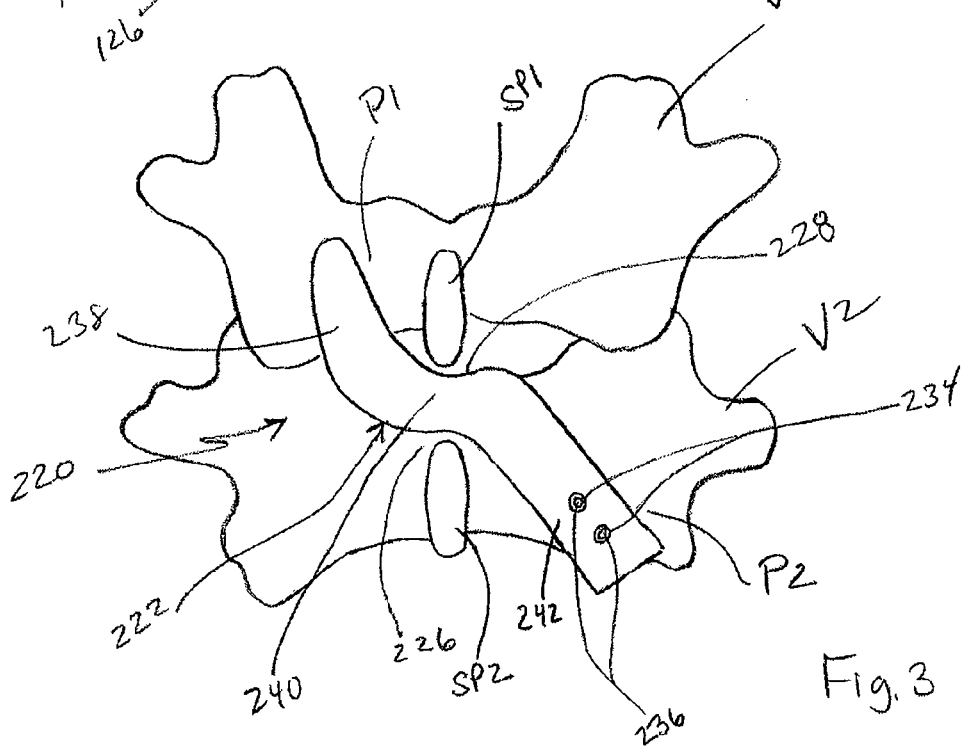
FIG. 3 is a posterior view of a portion of a spinal column and an implant according to an embodiment of the invention.
Figure 4:
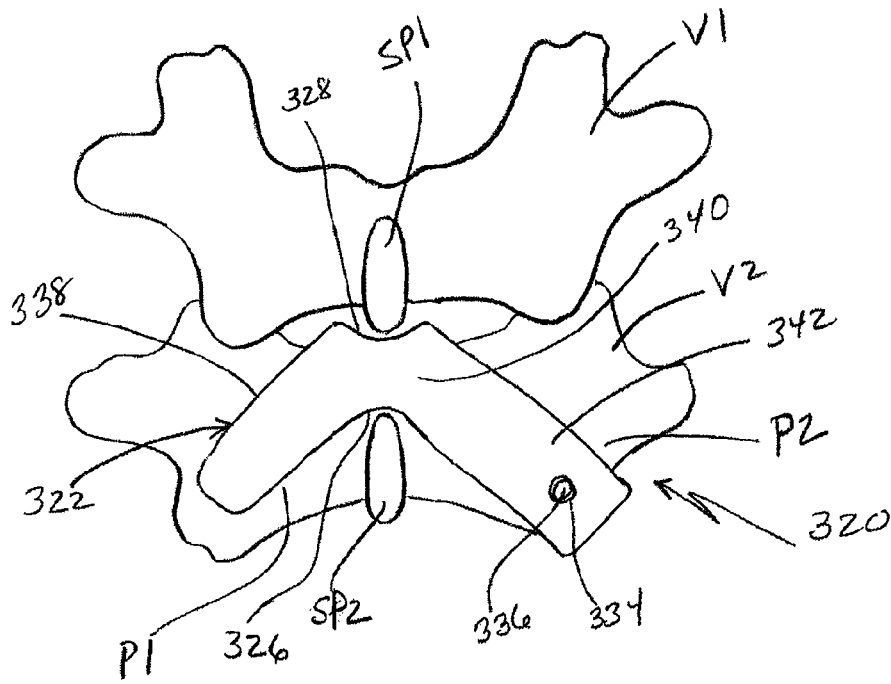
FIG. 4 is a posterior view of a portion of a spinal column and an implant according to an embodiment of the invention.

FIGS. 2-4 each illustrate a different embodiment of a medical device that can be at least partially disposed between adjacent spinous processes and coupled to a single pedicle within a spinal column. As shown in FIG. 2, a medical device 120 includes an implant 122 that has a curved shape and is shown with a portion disposed between a spinous process SP1 of a first vertebra V1 of a spinal column and a spinous process SP2 of a second vertebra V2 of the spinal column. The implant 122 includes a first outer surface 126 and a second outer surface 128. A portion of the first outer surface 126 can move in and out of contact with the spinous process SP2 during movement of the spinal column, and a portion of the second outer surface 128 can be in and out of contact with the spinous process SP1 of the first spinous process.

The implant 122 includes a first portion 138, a second portion 140 and a third portion 142. In this embodiment, the first portion 138 is configured to be disposed on a first side of the spinous processes SP1 and SP2, the second portion 140 is configured to be disposed at least partially between the spinous process SP1 and the spinous process SP2, and the third portion 142 is configured to be disposed on a second side of the spinous processes SP1 and SP2, opposite the first side, and configured to couple the implant 122 to a pedicle P2 of the vertebra V2. Thus, the implant 122 has a length such that a portion of the implant is disposed on opposite sides of the spinous processes SP1 and SP2, which helps maintain at least a portion (e.g., the second portion 140) of the implant 122 between the spinous processes SP1 and SP2. In some embodiments, the first portion 138 has a length such that it can be disposed adjacent a pedicle P1 of the vertebra V2.

The third portion 142 defines an opening 134, which in this embodiment is shown as an elongate slot. In other embodiments, the opening can be other shapes and sizes, such as, for example, round, square, rectangular, or triangular. The opening 134 can receive a coupling member 136 therethrough to couple the implant 122 to the pedicle P2 of the vertebra V2. The coupling member 136 can be, for example, a pin, nail, screw, or other fastening member.

In some embodiments, the coupling member 136 can couple the implant 122 to the pedicle P2 such that the implant 122 can move or slide relative to the coupling member 136 and/or pedicle P2 along a path defined by the opening 134. The implant 122 can also be coupled to the pedicle P2 such that the implant 122 can pivot about the coupling member 136 relative to the pedicle P2. For example, as a force is exerted from the spinous process SP1 and/or the spinous process SP2 on to the implant 122, the implant 122 can move along the path of the opening 134 and/or rotate or pivot relative to the coupling member 136 and/or pedicle P2.

In some embodiments, a coupling member fixedly couples the implant 122 to the pedicle P2 such that the implant 122 is substantially static relative to the pedicle P2 and the coupling member 146. In such an embodiment, when the spinal column moves between extension and flexion, and the implant 122 contacts one or both of the spinous process SP1 or the spinous process SP2, at least a portion of a force exerted on the implant 122 can be transferred to the pedicle P2. In some embodiments, the load or force is transferred asymmetrically from a point of contact with the spinous process (SP1 and/or SP2) to the coupling location at the pedicle P2. The implant 122 can also optionally or alternatively be formed with a flexible material such that when the implant 122 contacts the spinous process SP1 and/or the spinous process SP2, the implant 122 can flex or bend to accommodate movement of the spinal column.

FIG. 3 illustrates a medical device according to another embodiment. A medical device 220 includes an implant 222 that has a curved portion and a substantially straight portion, and is shown partially disposed between a spinous process SP1 of a first vertebra V1 of a spinal column and a spinous process SP2 of a second vertebra V2 of the spinal column. The implant 222 includes a first outer surface 226 and a second outer surface 228. A portion of the first outer surface 226 can move in and out of contact with the spinous process SP2 during movement of the spinal column, and a portion of the second outer surface 228 can move in and out of contact with the spinous process SP1. Although the first outer surface 226 is shown at least partially curved upward, and the second outer surface 228 is shown at least partially curved downward, the outer surfaces 226 and 228 can have different configurations. For example, the surfaces 226 and 228 can have more or less curvature than shown in FIG. 3, or can be substantially planar.

The implant 222 includes a first portion 238, a second portion 240 and a third portion 242. In this embodiment, the first portion 238 is configured to be disposed adjacent a pedicle P1 of the vertebra V1, the second portion 240 is configured to be disposed at least partially between the spinous process SP1 and the spinous process SP2, and the third portion 242 is configured to couple the implant 222 to a pedicle P2 of the vertebra V2. Similar to the previous embodiment, the implant 222 can have a length such that the first portion 238 is disposed outside of a space between the spinous processes SP1 and SP2, and on an opposite side of the spinous processes SP1 and SP2 from the third portion 242. This positioning can help maintain at least a portion of the implant 222 (e.g., second portion 240) between the spinous processes SP1 and SP2.

The third portion 242 defines two openings 234, which in this embodiment are substantially circular. As with the previous embodiments, the opening 234 can receive a coupling member 236 (e.g., screw, nail, pin) therethrough to couple the implant 222 to the pedicle P2 of the vertebra V2. The coupling member can fixedly couple the implant 222 to the pedicle P2, or pivotally couple the implant 222 to the pedicle P2 as described above. The openings 234 can be elongate slots or any other shape as described above.

As with the previous embodiment, when the spinal column moves between extension and flexion, and the implant 222 contacts one or both of the spinous process SP1 or the spinous process SP2, at least a portion of a force exerted on the implant 222 can be transferred to the pedicle P2. In some embodiments, the load or force is transferred asymmetrically from a point of contact with the spinous process (SP1 and/or SP2) to the coupling location at the pedicle P2. The implant 222 can also optionally or alternatively be formed with a flexible material such that when the implant 222 contacts the spinous process SP1 and/or the spinous process SP2, the implant 222 can flex or bend to accommodate movement of the spinal column.

FIG. 4 illustrates a medical device according to another embodiment. A medical device 320 includes an implant 322 that has two substantially straight portions and is shown disposed between a spinous process SP1 of a first vertebra V1 of a spinal column and a spinous process SP2 of a second vertebra V2 of the spinal column. The implant 322 includes a first outer surface 326 and a second outer surface 328. A portion of the first outer surface 326 can be in and out of contact with the spinous process SP2 during movement of the spinal column, and a portion of the second outer surface 328 can be in and out of contact with the spinous process SP1 of the first spinous process. In this embodiment, the second outer surface 328 is curved or concaved as shown in FIG. 4.

The implant 322 includes a first portion 338, a second portion 340 and a third portion 342. In this embodiment, the first portion 338 is configured to be disposed adjacent a pedicle P1 of the vertebra V2, the second portion 340 is configured to be disposed at least partially between the spinous process SP1 and the spinous process SP2, and the third portion 342 is configured to couple the implant 322 to a pedicle P2 of the vertebra V2. In alternative embodiments, the length of the implant 322 can vary. For example, the first portion 338 can have a shorter length than that represented in FIG. 4 such that it can be positioned on an opposite side of the spinous processes SP1 and SP2 from the third portion 342, but does not extend to the pedicle P1. The third portion 342 defines an opening 334 that can receive a coupling member 336 (e.g., screw, nail, pin) therethrough to couple the implant 322 to the pedicle P2 of the vertebra V2. The coupling member 336 can fixedly couple, or pivotally couple the implant 322 to the pedicle P2 as described above. The opening 334 can be elongate slots or any other shape as described above.

As with the previous embodiment, when the spinal column moves between extension and flexion, and the implant 322 contacts one or both of the spinous process SP1 and/or the spinous process SP2, at least a portion of a force exerted on the implant 322 can be transferred to the pedicle P2. In some embodiments, the load or force is transferred asymmetrically from a point of contact with the spinous process (SP1 and/or SP2) to the coupling location at the pedicle P2. The implant 322 can also optionally or alternatively be formed with a flexible material such that when the implant 322 contacts the spinous process SP1 and/or the spinous process SP2, the implant 322 can flex or bend to accommodate movement of the spinal column.

Figure 5:
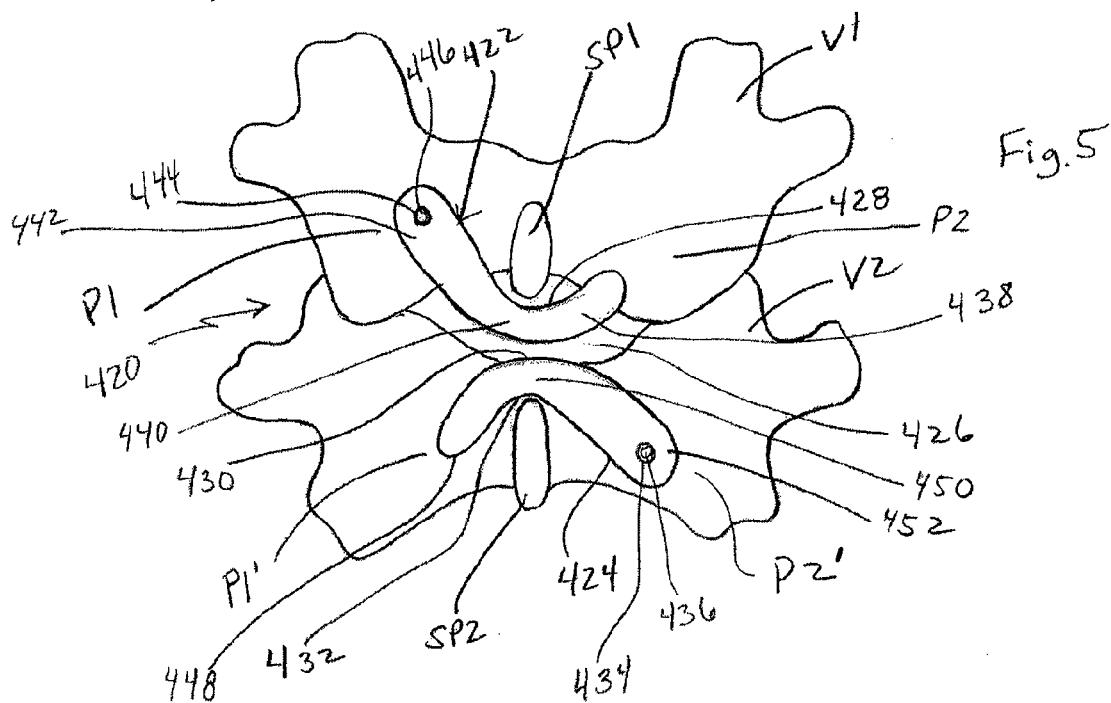
FIG. 5 is a posterior view of a portion of a spinal column and a pair of implants according to an embodiment of the invention.

FIG. 5 illustrates an embodiment of a medical device having two implants. A medical device 420 includes a first implant 422 and a second implant 424, each having a curved portion and a substantially straight portion, and each shown partially disposed between a spinous process SP1 of a first vertebra V1 of a spinal column and a spinous process SP2 of a second vertebra V2 of the spinal column. The implant 422 includes a first outer surface 426 and a second outer surface 428. A portion of the first outer surface 426 can move in and out of contact with an outer surface 430 of the second implant 424 during movement of the spinal column, and a portion of the second outer surface 428 can be in and out of contact with the spinous process SP1. The second implant 424 includes a second outer surface 432 that can be in and out of contact with the second spinous process SP2.

The implants 422 and 424 are similar to the implant 122 shown in FIG. 2. For example, the first implant 422 includes a first portion 438, a second portion 440 and a third portion 442. The first portion 438 is configured to be disposed on a first side of the spinous processes SP1 and SP2, the second portion 440 is configured to be disposed at least partially between the spinous process SP1 and the spinous process SP2, and the third portion 442 is configured to be disposed on a second side of the spinous processes SP1 and SP2, opposite the first side, and configured to couple the implant 422 to a pedicle P1 of the vertebra V1. In some embodiments, the first portion 438 has a length such that it can be disposed adjacent a pedicle P2 of the vertebra V1. The third portion 442 defines an opening 444, which can receive a coupling member 446 (e.g., screw, nail, pin) therethrough to couple the implant 422 to the pedicle P1 of the vertebra V1. As with the previous embodiments, the coupling member 446 can fixedly or pivotally couple the implant 422 to the pedicle P1, and the opening 444 can be any suitable shape or size.

Similarly, the second implant 424 includes a first portion 448, a second portion 450 and a third portion 452. The first portion 448 is configured to be disposed adjacent a pedicle P1' of the vertebra V2, the second portion 450 is configured to be disposed at least partially between the spinous process SP1 and the spinous process SP2, and the third portion 452 is configured to couple the implant 424 to a pedicle P2' of the vertebra V2. The third portion 452 defines an opening 434, that can receive a coupling member 436 (e.g., screw, nail, pin) therethrough to couple the implant 424 to the pedicle P2' of the vertebra V2. As with the previous embodiments, the coupling member 436 can fixedly or pivotally couple the implant 424 to the pedicle P2', and the opening 434 can be any suitable shape or size.

As with the previous embodiments, when the spinal column moves between extension and flexion, and the first implant 422 contacts the spinous process SP1 and/or the second implant 424, at least a portion of a force exerted on the implant 422 can be transferred to the pedicle P1. In some embodiments, the load or force is transferred asymmetrically from a point of contact with the spinous process SP1 to the coupling location at the pedicle P1 of the vertebra V1. Likewise, when the second implant 424 contacts the first implant 422 and/or the second spinous process SP2, at least a portion of a force exerted on the second implant 424 can be transferred to the pedicle P2' of the vertebra V2. The first implant 422 and/or the second implant 424 can also optionally or alternatively be formed with a flexible material such that when the implants 422, 424 contact the respective spinous processes SP1, SP2 and/or each other, the implants 422, 424 can flex or bend to accommodate movement of the spinal column.

Figure 6:
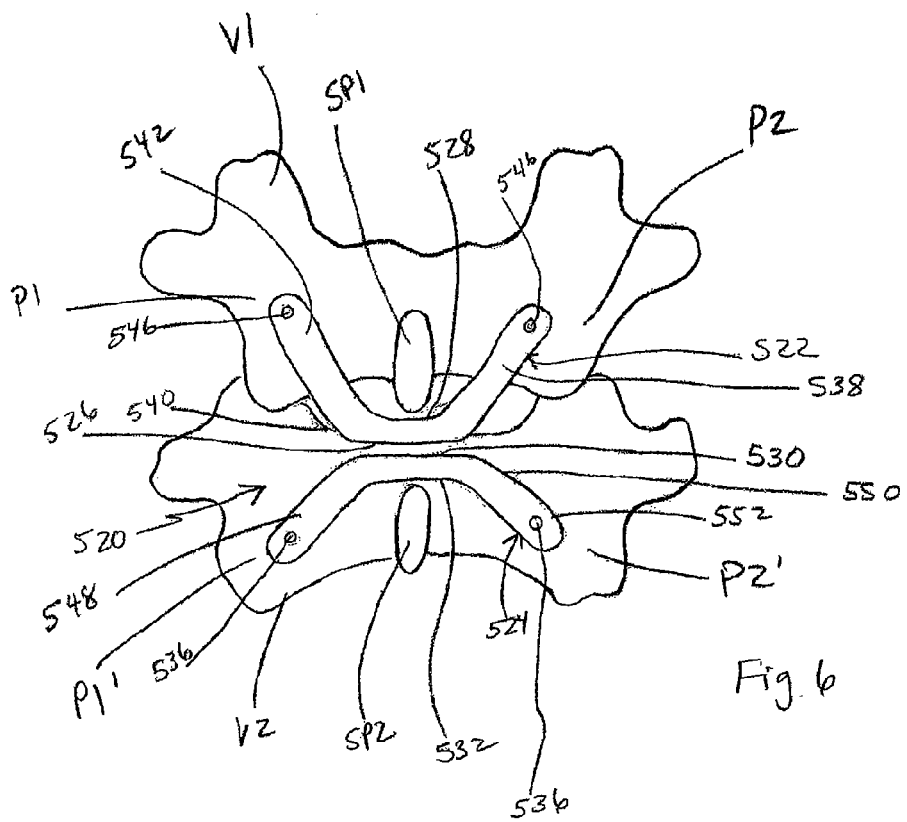
FIG. 6 is a posterior view of a portion of a spinal column and a pair of implants according to an embodiment of the invention.

FIG. 6 illustrates another embodiment of a medical device that includes two implants. A medical device 520 includes a first implant 522 and a second implant 524, each configured to be coupled to two pedicles of a respective vertebra. The first implant 522 is shown coupled to a first pedicle P1 and a second pedicle P2 of a vertebra V1 of a spinal column. The second implant 524 is shown coupled to a first pedicle P1' and a second pedicle P2' of a vertebra V2 of the spinal column. The first implant 522 includes a first outer surface 526 and a second outer surface 528. A portion of the first outer surface 526 can move in and out of contact with an outer surface 530 of the second implant 524 during movement of the spinal column, and a portion of the second outer surface 528 can be in and out of contact with a spinous process SP1 of the vertebra V1. The second implant 524 also includes a second outer surface 532 that can be in and out of contact with a second spinous process SP2 of the vertebra V2.

The first implant 522 includes a first portion 538, a second portion 540 and a third portion 542. The first portion 538 is configured to couple the implant 522 to the second pedicle P2 of the vertebra V1, the second portion 540 is configured to be disposed at least partially between the spinous process SP1 and the spinous process SP2, and the third portion 542 is configured to couple the implant 522 to the first pedicle P1 of the vertebra V1. The first portion 538 and the third portion 542 each define an opening (not shown), that can receive a coupling member 546 (e.g., screw, nail, pin) therethrough to couple the implant 522 to the pedicle P1 and pedicle P2 of the vertebra V1. As with the previous embodiments, the coupling members 546 can fixedly or pivotally couple the implant 522 to the pedicles P1 and P2, and the openings can be any suitable shape or size.

Similarly, the second implant 524 includes a first portion 548, a second portion 550 and a third portion 552. The first portion 548 is configured to couple the implant 524 to the pedicle P1' of the vertebra V2, the second portion 550 is configured to be disposed at least partially between the spinous process SP1 and the spinous process SP2, and the third portion 552 is configured to couple the implant 524 to the pedicle P2' of the vertebra V2. The first portion 548 and the third portion 552 each define an opening (not shown), that can receive a coupling member 536 (e.g., screw, nail, pin) therethrough to couple the implant 524 to the pedicles P1' and P2' of the vertebra V2. As with the previous embodiments, the coupling members 536 can fixedly or pivotally couple the implant 524 to the pedicles P1' and P2' of the vertebra V2, and the openings can be any suitable shape or size In this embodiment, when the spinal column moves between extension and flexion, and the first implant 522 contacts the spinous process SP1 and/or the second implant 524, at least a portion of a force exerted on the implant 522 can be transferred to the pedicle P1 and/or pedicle P2 of the vertebra V1. Likewise, when the second implant 524 contacts the first implant 522 and/or the second spinous process SP2, at least a portion of a force exerted on the implant 524 can be transferred to the pedicle P1' and/or the pedicle P2' of the vertebra V2. The first implant 522 and/or the second implant 524 can also optionally or alternatively be formed with a flexible material such that when the implants 522, 524 contact the respective spinous processes SP1, SP2 and/or each other, the implants 522, 524 can flex or bend to accommodate movement of the spinal column.

Figure 7:
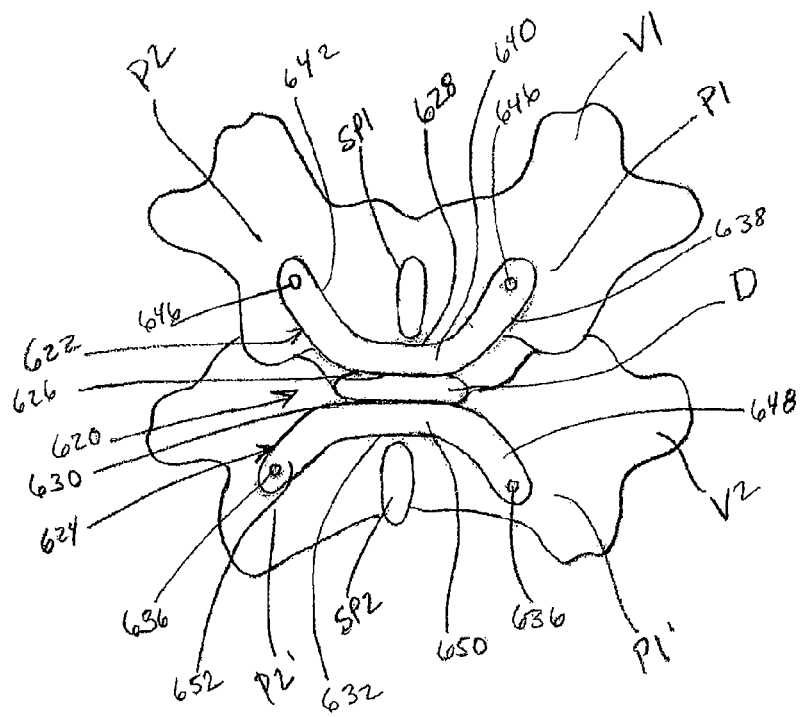
FIG. 7 is a posterior view of a portion of a spinal column and a pair of implants according to another embodiment of the invention with an interspinous-process device disposed between the pair of implants.

FIG. 7 illustrates another embodiment of a medical device that includes two implants and a third medical device that can be disposed between the two implants. A medical device 620 includes a first implant 622 and a second implant 624, each configured to be coupled to two pedicles of a respective vertebra. The first implant 622 is shown coupled to a first pedicle P1 and a second pedicle P2 of a vertebra V1 of a spinal column. The second implant 624 is shown coupled to a first pedicle P1' and a second pedicle P2' of a vertebra V2 of the spinal column. In this embodiment, an interspinous-process device D is disposed between the first implant 622 and the second implant 624. The interspinous-process device D is illustrated generically, but it should be understood that the interspinous-process device D can be a variety of different sizes, shapes and configurations.

The first implant 622 includes a first outer surface 626 and a second outer surface 628. A portion of the first outer surface 626 can move in and out of contact with an outer surface of the interspinous-process implant D during movement of the spinal column, and a portion of the second outer surface 628 can be in and out of contact with a spinous process SP1 of the vertebra V1. The second implant 624 includes a first outer surface 630 that can be in and out of contact with a surface of the interspinous-process device D, and a second outer surface 632 that can be in and out of contact with a second spinous process SP2 of the vertebra V2.

The first implant 622 includes a first portion 638, a second portion 640 and a third portion 642. The first portion 638 is configured to couple the implant 622 to the first pedicle P1 of the vertebra V1, the second portion 640 is configured to be disposed at least partially between the spinous process SP1 and the interspinous-process device D, and the third portion 642 is configured to couple the implant 622 to the second pedicle P2 of the vertebra V1. The first portion 638 and the third portion 642 each define an opening (not shown), that can receive a coupling member 646 (e.g., screw, nail, pin) therethrough to couple the implant 622 to the pedicle P1 and pedicle P2 of the vertebra V1. As with the previous embodiments, the coupling members 646 can fixedly or pivotally couple the implant 622 to the pedicles P1 and P2 of the vertebra V1, and the openings can be any suitable shape or size.

Similarly, the second implant 624 includes a first portion 648, a second portion 650 and a third portion 652. The first portion 648 is configured to couple the implant 624 to the pedicle P1' of the vertebra V2, the second portion 650 is configured to be disposed at least partially between the spinous process SP1 and the interspinous-process device D, and the third portion 652 is configured to couple the implant 624 to the pedicle P2' of the vertebra V2. The first portion 648 and the third portion 652 each define an opening (not shown), that can receive a coupling member 636 (e.g., screw, nail, pin) therethrough to couple the implant 624 to the pedicles P1' and P2' of the vertebra V2. As with the previous embodiments, the coupling members 636 can fixedly or pivotally couple the implant 624 to the pedicles P1 and P2 of the vertebra V2, and the openings can be any suitable shape or size In this embodiment, when the spinal column moves between extension and flexion, and the first implant 622 contacts the spinous process SP1 and/or the interspinous-process device D, at least a portion of a force exerted on the implant 622 can be transferred to the pedicle P1 and/or the pedicle P2 of the vertebra V1. Likewise, when the second implant 624 contacts the interspinous-process device D and/or the second spinous process SP2, at least a portion of a force exerted on the implant 624 can be transferred to the pedicle P1' and/or the pedicle P2' of the vertebra V2. The first implant 622 and/or the second implant 624 can also optionally or alternatively be formed with a flexible material such that when the implants 622, 624 contact the respective spinous processes SP1, SP2 and/or each other, the implants 622, 624 can flex or bend to accommodate movement of the spinal column.

Figure 8:
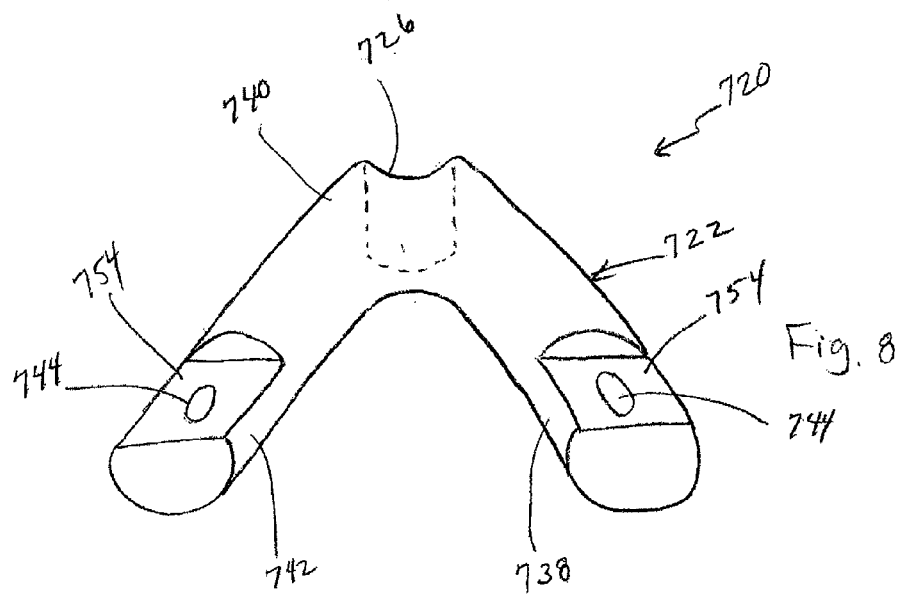
FIG. 8 is an end perspective view of an implant according to an embodiment of the invention.
Figure 9:
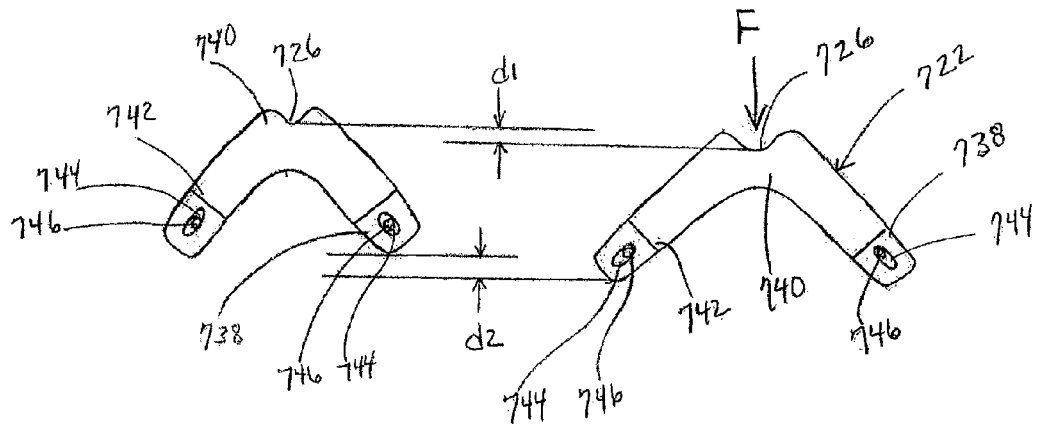
FIG. 9 is a front view of the implant of FIG. 8 shown in a first configuration and a second configuration.
Figure 10:
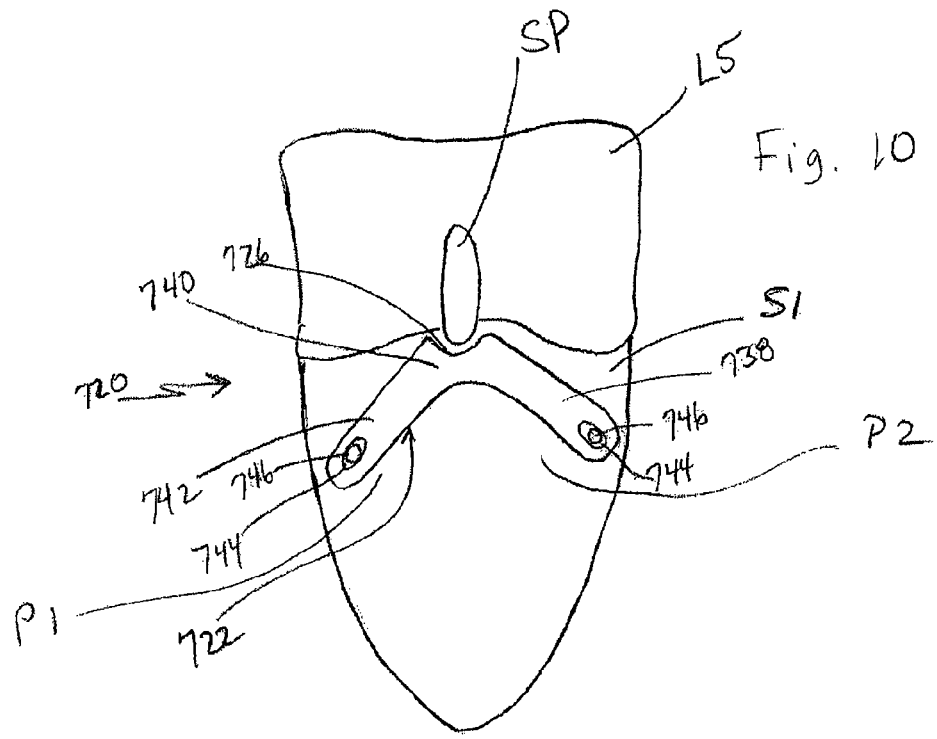
FIG. 10 is a posterior view of a portion of a spinal column and the implant of FIG. 8.

FIGS. 8-10 illustrate another embodiment of a medical device having an implant that can be coupled to two pedicles of a single vertebra. A medical device 720 includes an implant 722 having an outer surface 726 configured to be disposed beneath a spinous process. The outer surface 726 is concave in this example, but can alternatively be convex or substantially straight or planar. The implant 722 includes a first portion 738, a second portion 740 and a third portion 742. The first portion 738 is configured to couple the implant 722 to a first pedicle P1 of a first vertebra such as a sacral vertebra S1 as shown in FIG. 10. The second portion 740 is configured to be disposed at least partially beneath a spinous process SP of a second vertebra superior to the first vertebra, such as a L5 vertebra as shown in FIG. 10. The third portion 742 is configured to couple the implant 722 to a second pedicle P2 of the first vertebra (i.e., the L5 vertebra in this example).

As shown in FIG. 8, the first portion 738 and the third portion 742 each define a recessed portion 754 and an opening 744 defined within the recessed portion 754. The opening 744 is elongate and can receive a coupling member 746 (e.g., screw, nail, pin) (shown in FIGS. 9 and 10) therethrough to couple the implant 722 to the pedicle P1 and pedicle P2 of the first vertebra. As with the previous embodiments, the coupling members 746 can fixedly or pivotally couple the implant 722 to the pedicles P1 and P2, and the openings 744 can be any suitable shape or size.

The implant 722 can be formed with a semi-flexible or flexible material (e.g., polyetheretherketone) to allow the implant 722 to flex during movement of the spinal column. The coupling member 746 can couple the implant 722 to the pedicles such that the implant 722 can slide or move along a path defined by the elongate or slotted openings 744. The combination of the implant being formed with a semi-flexible material and having slotted openings 744 can provide an additional degree of freedom when the implant 722 is under a load. In alternative embodiments, the implant 722 can be formed with a semi-flexible or flexible material, and be fixedly coupled to the pedicles. In other alternative embodiments, the implant 722 is not formed with a flexible material, but includes slotted openings to allow the implant to move along a path defined by the openings. In some embodiments, the slotted openings are located on the implant such that they are oriented substantially vertical when the implant is disposed within the spinal column.

As shown in FIG. 9, as a force F is exerted on the implant 722 (e.g., from contact with a superior spinous process), the implant 722 can move and/or flex to accommodate movement of the spinal column. In this example, the second portion 740 of the implant 722 is shown moved a distance d1 when a force F is applied to the outer surface 726, and the first and second portions 738 and 742 are shown moved a distance d2. In some instances, the distance d1 and d2 will be substantially the same, and in other cases the distances d1 and d2 can be different.

Figure 11:
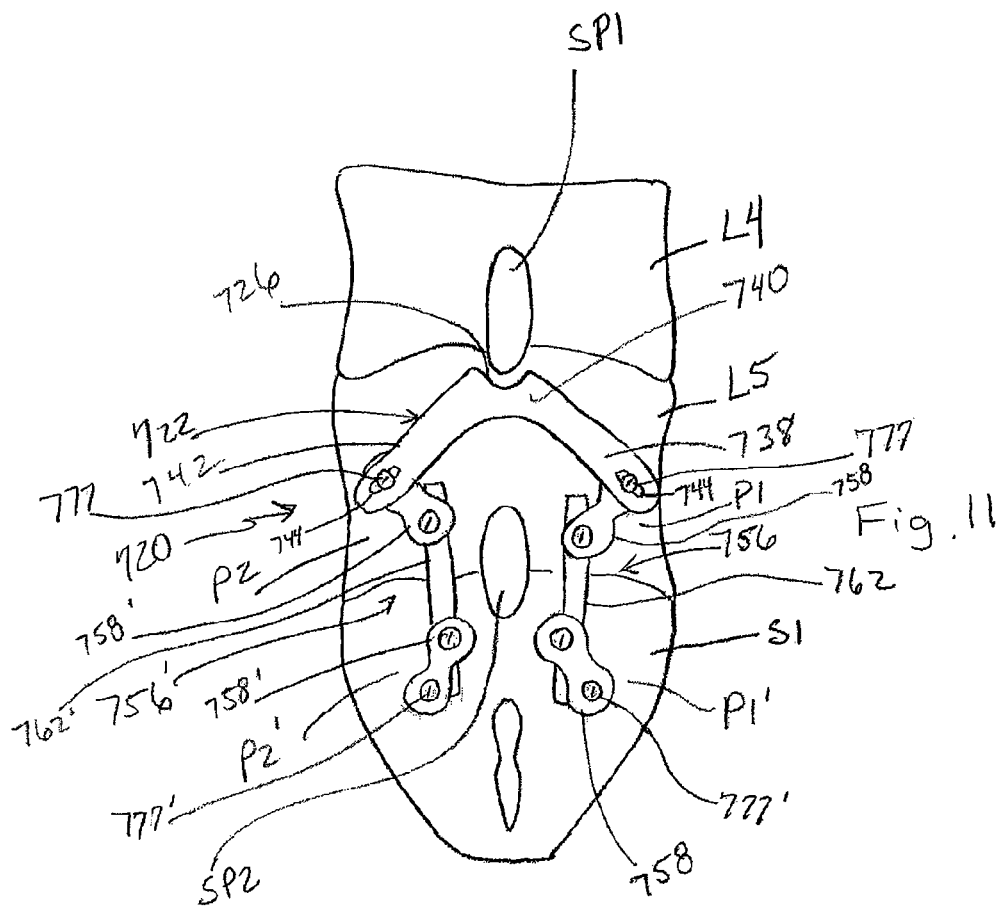
FIG. 11 is a posterior view of a portion of a spinal column, the implant of FIG. 8 and a fusion device according to an embodiment of the invention.

FIG. 10 illustrates the implant 722 disposed beneath the spinous process SP of the L5 vertebra and coupled to the pedicles P1 and P2 of the sacral vertebra S1. In such a position, the implant 722 can be used as an extension limiting device during extension of the spinal column. The implant 722 can also be used to off-load applied forces from the second vertebra, in this example the L5 vertebra, to the pedicles of the sacral vertebra S1. FIG. 11 illustrates the use of the implant 722 in combination with a pair of fusion devices 756 and 756' (described in more detail below). In such a use, the implant 722 and fusion devices 756, 756' can provide for a more gradual variation of the stiffness of the spinal column from one level to another, and can also be configured to limit extension at a given level of the spinal column. Although FIGS. 10 and 11 illustrate the implementation of the implant 722 for use between the L5 vertebra and the S1 sacral vertebra, the implant 722 as well as the fusion devices 756, 756' can be used at other levels within the spinal column.

As shown in FIG. 11, in this example, the implant 722 is coupled to a first pedicle P1 and a second pedicle P2 of the L5 lumbar vertebra such that the outer surface 726 of the implant 722 is disposed at least partially beneath a spinous process SP1 of the L4 lumbar vertebra. A first fusion device 756 is coupled to the first portion 738 of the implant 722, to a first pedicle P1 of the lumbar vertebra L5, and to a pedicle P1' of the sacral vertebra S1. A second fusion device 756' is coupled to the third portion 742 of the implant 722, to a pedicle P2 of the lumbar vertebra L5, and to a pedicle P2' of the sacral vertebra S1. Only the fusion device 756 is described in more detail below with reference to FIGS. 12-14, because the fusion device 756' is configured the same as the fusion device 756.

The fusion device 756 includes a pair of couplers 758, a pair of coupling members 760 and a rod 762. The fusion device 756 allows vertebrae to be coupled together regardless of the position of the anchor point because the position of each of the components of the fusion device 756 can be adjusted, as will be described in more detail below. As shown in FIGS. 12 and 13, each coupler 758 defines a pair of openings 763 and 764 that open into threaded cavities 770 and 771, respectively. A set screw (not shown) can be inserted through the opening 764 and engage the threaded cavity 771 to secure the coupler 758 to the rod 762. Another set screw (not shown) can be inserted through the opening 763 and engage the threaded cavity 770 to secure the coupler 758 to the coupling member 760. The coupler 758 also defines a through-hole 765 and a side opening 766. The through-hole 765 can receive the rod 762. A ball head 768 of the coupling member 760 can be side-loaded through the side opening 766 and disposed within an interior bore 767 of the coupler 758. As shown in FIG. 14, the ball head 768 defines a receiving portion 772 configured to matingly receive a tool to drive the coupling member 760 into a bone. The coupling member 760 also includes a threaded portion 769 that can be driven into a bone, such as a pedicle of a vertebra, to secure the fusion device 756 thereto. In alternative embodiments, the coupling member 760 can include spikes or protrusions that can be forced or driven into a bone, rather than a threaded portion.

As shown in FIG. 12, which illustrates a portion of the fusion device 756, the fusion device 756 defines 6 degrees of freedom at each coupler/rod/coupling member connection, as illustrated by the directions A, B, and C. Direction A is defined by the translation of the rod 762, direction B is defined by the adjustability of the height of the coupling member 760, and direction C is defined by the off-set of the coupler 758. The fusion device 756 can be assembled prior to coupling the fusion device 756 within a spinal column or to an implant. Alternatively, the fusion device can be assembled in situ or at least partially assembled prior to insertion into a spinal column.

An example of a method to secure the fusion device 756 within a spinal column will now be described. It should be understood that the fusion device 756' can be inserted into a spinal column in the same manner. In this example method, the fusion device 756 is secured within a spinal column without securing the fusion device to an implant, such as implant 722. The physician first drives (e.g., implants via rotation) a first coupling member 760 into a pedicle of a first vertebra, and a second coupling member 760 into a pedicle of a second adjacent vertebra. The coupling members 760 are driven partially into the pedicles such that at least the ball heads 768 are each protruding from a surface of the pedicles. The physician (or other medical practitioner or technician) can load a pair of couplers 758 onto the rod 762 and temporarily secure each of the couplers 758 to the rod 762 with a set screw 778 (shown in FIG. 15). The physician can then place the sub-assembly (rods 762 and couplers 758) into the patient so that each of the couplers 758 are offset from a ball head 768 of the coupling members 760. In this offset position, the side openings 766 of the couplers 758 are facing the ball heads 768 of the coupling members 760. The sub-assembly can then be translated or adjusted until each of the ball heads 768 of the coupling members 760 find the side opening 766 of the respective coupler 758 and are disposed within the interior bore 767 of the couplers 758.

Figure 15:
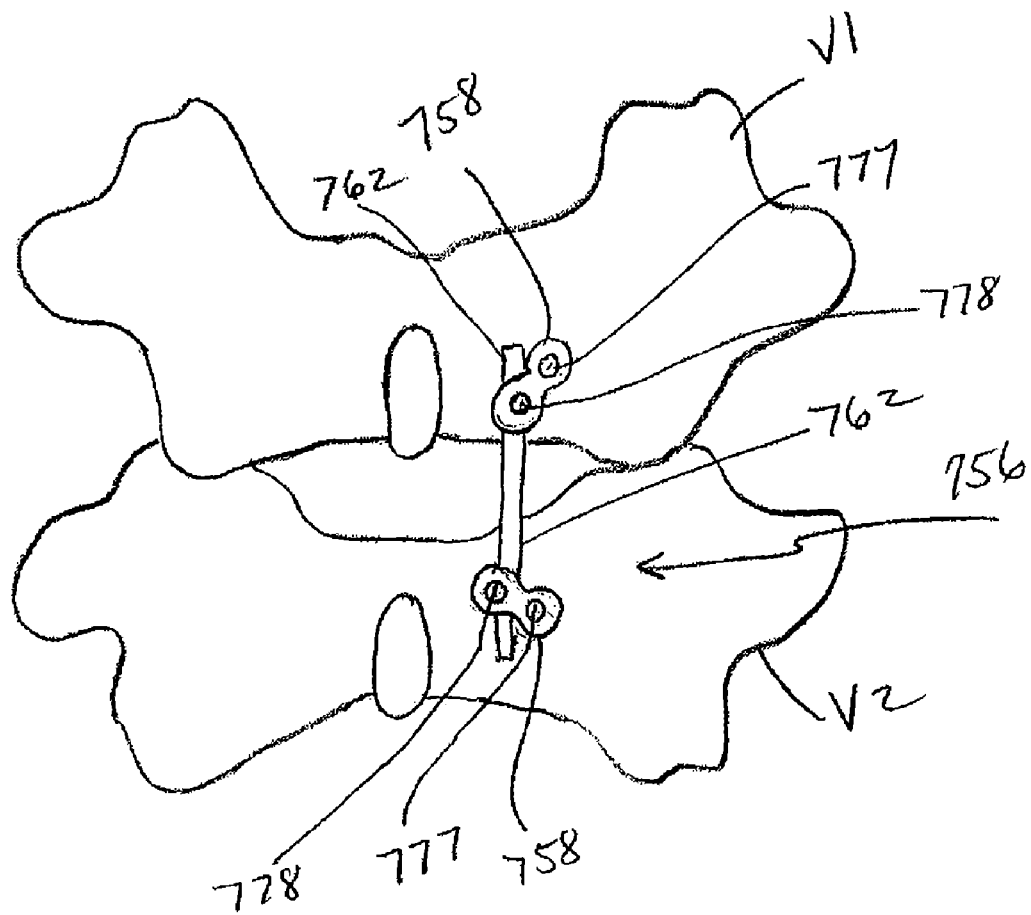
FIG. 15 is a posterior view of a portion of a spinal column, illustrating a fusion device according to an embodiment of the invention coupled to adjacent vertebra of the spinal column.

The physician can then, for example, drive the coupling members 760 further into the respective pedicle until each of the couplers 758 contacts the surface of the respective pedicle. The physician can manipulate the assembly and make any necessary adjustments to position the fusion device 756 in a desired location. For example, the rod 762 can slide or translate within the through-holes 765 to accommodate for the distance between the vertebra being coupled. As such, the rod 762 does not require cutting to size for a particular patient. The coupler 758 can also move relative the ball head 768 of the coupling member 760 for further adjustment. The fusion device 756 can then be secured to the pedicles with set screws 777, as shown in FIG. 15. FIG. 15 illustrates the fusion device 756 secured to a pedicle of a first vertebra V1 and a pedicle of a second vertebra V2. The set screws 778 (illustrated in FIG. 15) used to secure the rod 762 to the couplers 758 can also be tightened.

In alternative methods, the rod 762 and couplers 758 are not pre-assembled, but instead assembled after being placed within the patient. For example, the couplers 758 can be positioned relative to the ball head 768 of the coupling members 760 (having been driven into the pedicles), then the rod 762 can be inserted through the through-holes 765 of the couplers 758. In another alternative, the couplers 758 can be pre-assembled to the coupling members 760 prior to insertion into a spinal column. In such an embodiment, the receiving portion 772 of the coupling members 760 can be accessed through the openings 763 of the couplers 758 to drive the coupling members 760 into a bone. The rod 762 can then be inserted through the through-holes 765 of the couplers 758. Although only a single fusion device 756 is shown in FIG. 15, a method can include securing more than one fusion device within the spinal column. For example, a pair of fusion devices can be secured to two adjacent vertebra. In other cases, one or more fusion devices can be secured at a first level of the spinal column and one or more fusion devices can be secured at a second level of the spinal column.

To couple the fusion devices 756 and 756' within a spinal column together with an implant, as shown in FIG. 11, the physician can place the implant 722 in a desired position within the spinal column to determine a location for insertion of the coupling members 760 (not shown in FIG. 11). The coupling members 760 can then be driven into the pedicles P1, P2, P1' and P2' in the same manner as described above. A first sub-assembly of a rod 762 and couplers 758 can be placed relative to the coupling members 760 coupled to pedicles P1 and P1', and a second sub-assembly of a rod 762' and couplers 758' can be placed relative to the coupling members 760 coupled to pedicles P2 and P2'. In this example, the implant 722 can then be repositioned beneath the spinous process SP1 and coupled to the couplers 758 and 758' that are positioned adjacent the pedicles P1 and P2, respectively, of the L5 vertebra. For example, the couplers 758 and 758' can be placed within the recessed portions 754 (shown in FIG. 8) of the implant 722. The coupling members 760 can then be driven further into the pedicles as described above. For example, the receiving portion 772 of the ball heads 768 of the coupling members 760 can be accessed through the openings 744 of the implant 722. Set screws 777 can then be placed within the openings 763 of the couplers 758, 758' to at least temporarily secure the implant 722 to the couplers 758, 758'.

Similar to as described above, the physician can manipulate the fusion devices 756 and 756', and the implant 722 and make any necessary adjustments to position the fusion devices 756 and 756' and implant 722 in a desired location. The rods 762 and 762' can each be translated within the through-holes (not shown in FIG. 11) to accommodate for the distance between the vertebra L5 and the vertebra S1. The couplers 758 and 758' can also move relative the ball heads 768 of the coupling members 760 for further adjustment. The slotted or elongate openings 744 of the implant 722 can also provide additional adjustment. After manipulating the implant 722 and fusion devices 756, 756' into a desired position, the set screws 777 can be tightened to secure the implant 722 to the couplers 758 and 758', and the fusion devices 756 and 756' to the pedicles P1 and P2 of the L5 vertebra. Set screws 777' (shown in FIG. 11) can be tightened to secure the fusion devices 756 and 756' to the pedicles P1' and P2' of the S1 vertebra.

In alternative embodiments, other types of fusion devices not specifically described and illustrated herein can be used in conjunction with a spinous process implant. Thus, a fusion device can have a variety of different shapes sizes and configurations. For example, a fusion device can include multiple components coupled together, or be a single component configured to be coupled to a first vertebra a second adjacent vertebra. A fusion device can be fixedly or movably coupled (e.g., pivotally or slidably) to a spinous process implant and/or to a vertebra.

Figure 16:
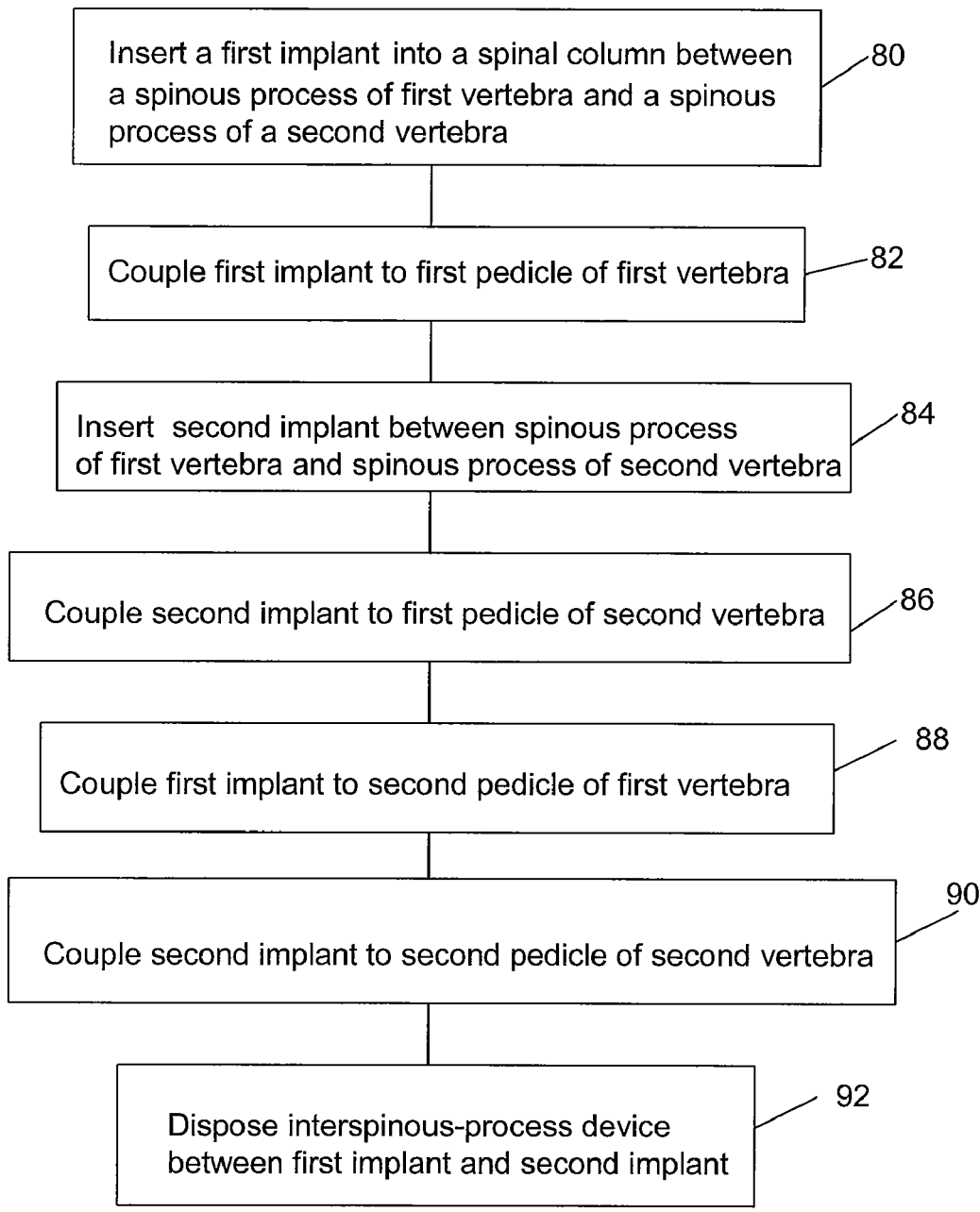

FIG. 16 is a flowchart illustrating a method for coupling implants to pedicles of a spinal column according to an embodiment of the invention. A method includes at 80 inserting a first implant into a spinal column such that at least a portion of the first implant is disposed between a spinous process of a first vertebra and a spinous process of a second vertebra. In some embodiments, the first implant is percutaneously inserted into the spinal column. At 82, the first implant is coupled to a first pedicle of the first vertebra of the spinal column. The first implant can be fixedly or pivotally coupled to the first pedicle of the first vertebra. For example, in some embodiments, the first implant can be threadedly coupled to the pedicle, with, for example, a bone screw.

At 84, a second implant is inserted into the spinal column and is at least partially disposed between the spinous process of the first vertebra and the spinous process of the second vertebra. In some embodiments, the second implant is percutaneously inserted into the spinal column. At 86, the second implant is coupled to a first pedicle of the second vertebra of the spinal column. As with the first implant, the second implant can be fixedly or pivotally coupled to the first pedicle of the second vertebra, and can in some embodiments be threadedly coupled to the pedicle with, for example, a bone screw.

In some embodiments, at least a portion of an outer surface of the first implant can contact at least a portion of an outer surface of the second implant when the spinal column is in extension. For example, such contact can be at a location between the first spinous process and the second spinous process. In some embodiments, the outer surface of the first implant and the outer surface of the second implant can be at a spaced distance from each other when the spinal column is in flexion. In some embodiments, at least a portion of a force exerted on the first implant or the second implant from contact with a spinous process and/or from contact with each other will be transferred to the pedicle of the vertebra to which the implant is coupled.

At 88, in some embodiments, the first implant is coupled to a second pedicle of the first vertebra, and at 90 the second implant is coupled to a second pedicle of the second vertebra. The first implant and the second implant can each be coupled to the respective second pedicle of the first and second vertebra, respectively, either fixedly or pivotally. At 92, in some embodiments, an interspinous-process device can be disposed between the first and second implants, and used in conjunction with the first and second implants to limit extension of the spinal column.

Although the above method describes the implantation of two implants to adjacent vertebra, it should be understood that steps 84-92 are optional. For example, a method can alternatively include only 80 and 82 described above, when only a single implant is being implanted within a spinal column (see, e.g., FIGS. 2-4).

FIG. 17 illustrates a method for coupling an implant within a spinal column according to an embodiment of the invention. At 81, a first portion of an implant is disposed below a spinous process of a lumbar vertebra of a spinal column. At 83, a second portion of the implant is coupled to a sacral vertebra of the spinal column. For example, the sacral vertebra can be a S1 sacral vertebra, and the lumbar vertebra can be a L5 lumbar vertebra. When the implant is coupled to the sacral vertebra, the implant can limit extension of the spinal column. At 85, a third portion of the implant can optionally be coupled to the sacral vertebra on an opposite side of a mid-line of the spinal column from the second portion of the implant. The implant can be fixedly coupled to the sacral vertebra, with, for example, with a pedicle screw. In some embodiments, the implant is pivotally coupled to the sacral vertebra.

FIG. 18 is a flowchart illustrating another method for coupling an implant within a spinal column. At 91, a first portion of an implant is disposed beneath a spinous process of a first vertebra of a spinal column. At 92, a second portion of the implant is coupled to a second vertebra of the spinal column adjacent the first vertebra. At 93, a first portion of a fusion device, as described herein, is coupled to the second portion of the implant. The first portion of the fusion device can be fixedly or pivotally coupled to the second portion of the implant. At 94, a second portion of the fusion device is coupled to a third vertebra of the spinal column adjacent the second vertebra. The second portion of the fusion device can be fixedly or pivotally coupled to the third vertebra.

At 95, a third portion of the implant can be coupled to the second vertebra. At 96, a second fusion device can be coupled to the third portion of the implant and at least one of the second vertebra or the third vertebra. In some embodiments, the first vertebra is, for example, a L4 lumbar vertebra; the second vertebra is, for example, a L5 lumbar vertebra; and the third vertebra is, for example, a S1 sacral vertebra.

The implants and fusion devices for any of the embodiments can be formed with any suitable material used for such medical devices. For example, the implants or components of a fusion device can each be formed with biocompatible metal materials, such as stainless steel, titanium, titanium alloy, surgical steel, metal alloys, or suitable biocompatible plastic materials, such as various polymers, polyetheretherketone (PEEK), carbon fiber, ultra-high molecular weight (UHMW) polyethylene, etc., or various elastic materials, flexible materials, various rubber materials, or combinations of various materials thereof. In addition, any of the embodiments of an implant or fusion device can be formed with one or more compliant materials.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having a combination or sub-combination of any features and/or components from any of embodiments as discussed above. For example, the various embodiments of an implant are merely examples, as an implant according to the invention can have other shapes, sizes and configurations. For example, an implant can be symmetrical, such as, for example, the implants 522 and 524, or an implant can be non-symmetrical, such as for example, the implants 122 and 222. In addition, although the embodiments above are primarily described as being spinal implants configured to be coupled to a pedicle of a vertebra, in alternative embodiments, the implants are configured to be coupled to other bone, tissue or other bodily structure.

Any of the various embodiments of an implant can be configured such that during extension of the spinal column, the implant is engagable with, or has a spaced distance to, either another implant coupled to an adjacent spinous process or to an interspinous-process implant. Similarly, any of the embodiments of an implant can be configured such that during flexion of the spinal column, the implant is engagable with, or is at a spaced distance from, either another implant coupled to an adjacent spinous process or to an interspinous-process implant. In some embodiments, an implant is engagable and remains in contact with another implant or an interspinous-process implant during both flexion and extension. In other embodiments, an implant is at a spaced distance from another implant or an interspinous-process implant during both flexion and extension.

Various combinations of the different embodiments of an implant can be implanted within a spinal column. For example, a procedure can include coupling one implant to pedicles associated with one level of a spinal column, or can include two or more implants each being coupled within the same level or at different levels within the spinal column. Where multiple implants are used, the implants can have the same or different configurations.

The fusion devices described herein can be used alone, or in combination with a variety of different configurations of an implant. The fusion devices can be used with more than one implant. For example, one or more fusion devices can be coupled to a first implant that is coupled to a first vertebra of a spinal column and a second implant that is coupled to a second vertebra.

What is claimed is:

1. An apparatus, comprising:
   an implant having an arcuate shaped surface configured to contour at least one spinous process of a vertebrae including a first portion, a second portion and a third portion disposed in a longitudinal series and connected in a fixed configuration;
   the first, second, and third portions of the implant configured relative to each other such that, when the implant is disposed between first and second adjacent vertebrae of a human spinal column, the implant is configured to be disposed with:
      the first portion disposed adjacent to a pedicle of a first vertebra of a spinal column and extending superiorly from an interspinous process gap formed by adjacent upper and lower spinous processes, associated with the first and second vertebrae on a first lateral side of the vertebrae; the first portion extending more superiorly than any other portion of the implant;
      the second portion of the implant disposed through the interspinous process gap;
      the third portion pivotally coupled to a pedicle of the second vertebra and extending inferiorly from the interspinous process gap on a second lateral side of the vertebrae;
   the implant configured to transfer asymmetrically to the second vertebra at least a portion of a force exerted on the implant from one of the spinous processes.

2. The apparatus of claim 1, wherein the third portion of the implant is configured to be fixedly coupled to the pedicle of the second vertebra.

3. The apparatus of claim 1, wherein the implant is formed of a flexible material, the implant configured to flex when a force is exerted on the implant from one of the spinous processes.

4. The apparatus of claim 1, wherein the third portion of the implant is pivotally coupled to the pedicle of the second vertebra.

5. The apparatus of claim 1 wherein the implant includes an outer surface, at least a portion of the outer surface configured to move in and out of contact with the spinous process of the first vertebra during movement of the spinal column between flexion and extension.

6. The apparatus of claim 1 wherein the implant includes a first surface and a second surface, the first surface configured to move in and out of contact with the spinous process of the first vertebra and a second surface configured to move in and out of contact with the spinous process of the second vertebra during movement of the spinal column between flexion and extension.

7. The apparatus of claim 1 wherein the third portion includes at least one opening configured to receive a coupling member therethrough to couple the implant to the pedicle of the second vertebra.

8. The apparatus of claim 1 wherein the first portion curves superiorly relative to the second portion.

9. The apparatus of claim 8 wherein the third portion is substantially straight and extends inferiorly at a non-orthogonal angle relative to the second portion.

10. The apparatus of claim 1 wherein when the implant is disposed between first and second adjacent vertebrae, the implant is configured such that no portion of the implant overlaps the upper spinous process on the second lateral side.

11. The apparatus of claim 1 wherein a centerline extends through the first, second, and third portions, wherein the centerline curves in a first direction proximate the intersection of the first and second portions and curves in an opposite second direction proximate the intersection of the second and third portions.

12. An apparatus, comprising:
  an implant having an arcuate shaped surface configured to contour at least one spinous process of a vertebrae including a first portion, a second portion and a third portion disposed in a longitudinal series and connected in a fixed configuration;
  the first, second, and third portions of the implant configured relative to each other such that, when the implant is disposed between first and second adjacent vertebrae of a human spinal column, the implant is configured to be disposed with:
    the first portion disposed adjacent to a first pedicle of a first vertebra of a spinal column;
    the second portion of the implant disposed through the interspinous process gap;
    the third portion pivotally coupled to a second pedicle of the first vertebra and;
  the implant configured to transfer asymmetrically to the second vertebra at least a portion of a force exerted on the implant from one of the spinous processes.

* * * * *